United States Patent [19]

Spector

[11] 4,042,682
[45] Aug. 16, 1977

[54] ENDOGENOUS MORPHINE-LIKE COMPOUND

[75] Inventor: Sidney Spector, Livingston, N.J.

[73] Assignee: Hoffmann-La Roche Inc., Nutley, N.J.

[21] Appl. No.: 674,467

[22] Filed: Apr. 7, 1976

[51] Int. Cl.$^2$ .................. A61K 35/30; A61K 31/485; C07D 489/00
[52] U.S. Cl. ..................................... 424/95; 260/285; 424/260
[58] Field of Search ................... 424/95, 260; 260/285

[56] References Cited

U.S. PATENT DOCUMENTS 3,047,465   7/1962   Heath et al. ........................... 424/95

Primary Examiner—Sam Rosen
Attorney, Agent, or Firm—Samuel L. Welt; George M. Gould

[57] ABSTRACT

A morphine-like compound (MLC) can be extracted from the brain of various species by utilizing morphine specific antibodies. MLC shows great similarities to morphine in immunological, chemical and chromatographic tests. The compound has biological activity as it inhibits the electrically induced contractions both of the guinea pig ileum and mouse vas deferens but the inhibition is not reversed by naloxone or naltrexone.

2 Claims, No Drawings

ENDOGENOUS MORPHINE-LIKE COMPOUND

BACKGROUND OF THE INVENTION

Drug interactions with tissue receptors are believed to be highly specific and pharmacologically active substances exert their biological effects by interacting with these tissue receptors. Another very specific interaction is the immune reaction. The interaction of antibodies with a protein antigen is a very complex one as each antigenic molecule has many determinant groups with which the antibody can bind. Drugs, because of their low molecular weight, do not generally yield antibodies but they can be made to act as haptenic moieties when conjugated to carrier proteins. Some of the antibodies thus generated recognize various parts of the haptenic group. Thus, it should be possible to develop antibodies which have a confirmational complementarity to a drug very much like the receptor. The antibodies could then be used to bind the endogenous ligand for the receptor.

There is considerable evidence which suggests that the analgesic effects produced by the opiates are mediated via discrete functional receptors. This evidence includes the rigid steric requirements necessary for analgesic activity, the ability of naloxone to to antagonize the pain suppressant effects of all the structurally diverse opiates, recent demonstration of the presence in nervous tissue of saturatable, high affinity stereospecific binding sites for opiates which can be blocked by naloxone, and of a peptide with morphine-like properties.

It is thus reasonable to assume that any substance with morphine-like biological properties should bear, to at least some extent, structural similarities to morphine. In order for the molecule to elicit an effect, it must first bind or interact with the receptor. Thus, there is a recognition by the receptor of the agonist. Antibodies have previously been disclosed (Spector and Parker, Science, 168,1347 [1970]) toward the haptenic molecule morphine by conjugating it to the protein carrier bovine serum albumin (BSA). The antibodies produced by this immunogen recognize various determinant portions of the morphone molecule specifically (Spector, J. Pharmacol. Exp. Ther. 178, No. 2,253 [1970]).

DESCRIPTION OF THE INVENTION

The present invention relates to the isolation of an endogenous substance having morphine-like biological and immunological properties from mammalian brain tissue. This morphine-like compound (MLC) is isolated from methanol extracts of brain tissue homogenates by utilizing morphine specific antibodies generated by a carboxymethylmorphine immunogen. MLC will bind to these antibodies and the resulting MLC-antibody conjugate can be separated from the tissue extract solution by ammonium sulfate precipitation. Separation of the MLC from the anitbody is readily achieved by denaturizing the protein by heat, followed by ultrafiltration of the solution through a filter having a one thousand molecular weight cutoff. The MLC is found in the filtrate.

Methanol extracts of homogenates of discrete regions were tested for the presence of MLC by utilizing a radiommunoassay based on competition with $^3$H-dihydromorphine for binding onto morphine antibodies. As seen from the results summarized in Table 1 below, MLC has a discrete distribution in both cat and rabbit brain.

TABLE I

DISTRIBUTION OF MLC IN THE BRAIN OF RABBITS AND CATS

| Brain Region | Rabbit ng/g | Cat ng/g |
| --- | --- | --- |
| Caudate | 33 ± 10 (10) | 24 ± 7 (5) |
| Hypothalmus | 14 ± 4 (2) | 12 ± 6 (3) |
| Cerebellum | 12 ± 3 (9) | 14 ± 4 (5) |
| Hippocampus | 8 ± 3 (4) | 5 ± 2 (3) |
| Mid Brain | 4 ± 1 (3) | 2.7 ± 1 (3) |
| Pons and Medulla | 4 ± 1 (2) | |
| Cortex | 2 ± 1 (5) | 1.5 ± 0.7 (2) |

The various regions of brain were homogenized in three volumes of ice cold methanol as described in methods. An aliquot of the supernatent was then tested for its ability to inhibit the binding of $^3$H dihydromorphine to morphine antibodies. The data was expressed as morphine immuno equivalents. The number of individual determinations is indicated in parenthesis.

In rabbit, the caudate contained the highest concentration of morphine immunoequivalents, 33ng/g tissue; the hypothalmus and cerebellum contained approximately equal concentrations of 14 and 122 ng/g respectively and the hippocampus 8 ng/g. the cortex contained the smallest amounts with approximately 2 ng/g. Similar distributions were obtained in cat brain. MLC activity was also present in brains of guinea pig, rat, pig and beef.

In order to eliminate the possibility that the MLC activity was a consequence of an interaction between the labeled dihydromorphine and MLC, thereby preventing the labeled compound from reacting with antibody, additional studies were carried out. Such studies demonstrated that MLC plus non-radioactive morphine yielded an additive inhibition in the radioimmunoassay that was independent of the sequence of addition. This is not what one would expect if MLC binds the labeled dihydromorphine and would rule out this possibility.

Another possibility for an alternate explanation for the observed activity of MLC was that MLC could have been absorbed onto serum protein in a nonspecific manner and then precipitated with ammonium sulfate. To test this possibility MLC was incubated with normal serum in the absence of morphine specific antibody. Under these conditions the pellet obtained after precipitation with ammonium sulfate did not contain MLC.

Since morphine was conjugated to BSA to produce the immunogen, the possibility existed that the endogenous substance was binding to that portion of the antibody which was the recognition site for the BSA. This possibility was ruled out by showing that other haptens such as reserpine, melatonin and propranolol, also coupled to BSA, yielded antigen which did not interact with MLC. It is of interest that antibodies to naloxone, a specific antogonist of morphine, did react with MLC. However, the concentration in terms of naloxone immunoequivalent was seven times less than the one obtained in morphine units.

All the above suggests that MLC inhibits the radioimmunoassay by competing for binding sites specific for morphine on the antibody.

METHODS

The method for purfication of the morphine-like compound (MLC) is as follows.

The various areas of the brain from rabbit and cat were homogenized in three volumes of ice cold methanol containing $10^{-2}$M ascorbic acid with a Teflon homogenizer and kept at 4° C. for 30-45 minutes. Each sample was then centrifuged at 4° C. in a Beckman RC2-B centrifuge at 30,000 Xg for 45 minutes. The supernatent was carefully removed, diluted with three volumes of double distilled water and lyophilized. The dried sample was redissolved in a volume of water 10-20% of its original methanol volume and an aliquot was assayed for morphine-like activity by testing for its ability to compete with dihydromorphine for specific binding sites on antibodies generated in rabbits against carboxymethylmorphine immunogen. The concentration of morphine-like compound (MLC) is expressed as morphine immuno equivalents. This has been determined by comparing the degree of inhibition of binding of $^3$H-dihydromorphine produced by non-radioactive morphine with the degree of inhibition of binding produced by MLC. Following the determination of MLC concentration in the methanol extract, morphine antiserum was added to the reconstituted sample in an amount ten times that required to bind 50% of the MLC. This amount of antiserum was capable of binding all of the MLC activity. Normal rabbit serum was then added to achieve a final serum concentration of 15% and the solution was allowed to incubate overnight at 4° C. An equal volume of saturated ammonium sulfate was added as described by Farr, J. Infect. Dis. 103,239 (1958) and the solution was vigorously shaken and allowed to stand for 30 minutes at 4° C. This leads to precipitation of the antibody-MLC complex along with globulins. After centrifugation at 13,000 Xg at 4° C. for 30 minutes, the supernatent fluid was discarded. The pellet was washed once with 50% saturated ammonium sulfate, centrifuged at 13,000 Xg at 4° C. for 30 minutes and then resuspended in a volume of distilled water which was 5-10% of the orginal volume of methanol. The suspension was then dialyzed in tubing which has a 3000 molecular weight cutoff. This was done with vigorous stirring against 2000 volumes of distilled water at room temperature for two hours. The material in the dialysis bag was transferred to a test tube which was then placed into boiling water for five minutes. The heat precipitated antibody was separated from the soluble MLC by centriugation at 30,000 Xg at 4° C. for 45 minutes. The supernatent was then filtered through a UM-2 filter (one thousand molecular weight cutoff) which had previously been washed with 50 ml. distilled water under three atmospheres of pressure of nitrogen at 4° C. The filtrate was either used immediately or lyophilized and stored at 4° C. Of the total activity measured in the initial methanol extracts between 60 to 75% was recovered at the final step of purification.

For determining the distribution of MLC in the central nervous system crude methanol extracts were assayed without any additional purification. The concentrations were calculated by using a standard curve which had been constructed in the presence of an equal amount of methanol. Studies on the physical and chemical properties of MLC were performed on material obtained through the entire extraction procedure. In experiments involving the effects of peptidases, the solution was subsequently placed in boiling water for ten minutes to destroy the enzymatic activity prior to radioimmunoassay. Following incubation with oxidizing agents an excess of $K_2S_2O_5$ was added to destroy excess oxidant.

For chromatographic studies MLC and morphine were spotted separately and co-chromatographed on silica gel thin layer plates. These were developed in four different solvent systems, n-butanol-acetic water (4:1:1), chloroform-acetone-diethylamine (5:4:1), chloroform-diethylamine (9:1) and n-butanol-benzene-methanol-water (15:10:60:15). After drying in a warm oven, each chromatogram was analyzed under ultraviolet light and by staining with ferric chloride ferricyanide mixture, a phenol reagent.

Biological studies were carried out on both the guinea pig ileum and mouse vas deferens. The ileum of the guinea pig was mounted and stimulated by transmural electrical stimulation as described by Paton, Br. J. Pharmacol. 11, 119 (957); the intraluminal electrode was made the anode. Rectangular current pulses of 0.2 m sec. duration and of sufficient strength to produce a maximal response to a single shock were applied to the electrodes once every 10 seconds with a Grass model S88 stimulator. Stimuli were continuously monitored on an oscilloscope which was connected across the electrodes. The isometric contractions of the gut were recorded via a Grass FT 03 force transducer on a Grass polygraph. The resting tension was fixed at 1 gr. The temperature of the 5 ml. organ bath was kept constant at 37° C. All of the experiments were made on pieces of ileum suspended in a modified Krebs' solution at pH 7.4 with the following composition (in millimolar concentrations): NaCl, 118; KCl, 4.7; $CaCl_2$, 2.5; $MgCl_2$, 1.2; $NaH_2PO_4$, 1.2; $NaHCO_3$, 25; glucose, 11; choline chloride, 0.29. A mixture of 95% $O_2$ and 5% $CO_2$ was bubbled through the buffer for oxygenation.

Both vas deferentia were removed from 25 g. mice, tied together at both ends, mounted in a 3 ml. organ bath between 2 parallel silver electrodes and stimulated as described above for the guinea pig ileum. The buffer used was a modified Krebs' solution at pH 7.4 with the following composition (in millimolar concentration): NaCl 118; KCl 4.75; $CaCl_2$ 2.54; $MgSO_4$ 1.27; $KH_2PO_4$ 0.93; $NaHCO_3$ 25.0; glucose 11.0. The same gas mixture was used for oxygenation, and the buffer was maintained at 34° C.

BIOLOGICAL ACTIVITY

Stimulated guinea pig ileum and mouse vas deferens are two peripheral neuroeffector junctions that are sensitive to morphine in a narcotic specific fashion. The MLC was, therefore, tested for biological activity on both of these systems. MLC at a dose of 0.2 ng/ml of morphine immuno equivalents produced a transient inhibition of electrically induced contractions of the guinea pig ileum. The onset of inhibition occurred within 10 seconds and usually reached its maximum of about 40% inhibition within 30 seconds after which there was partial recovery. A concentration of 0.1 ng/ml produced a 20% inhibition of contraction. This demonstrates a parallelism between the RIA activity and biological activity. Morphine elicited a 40% inhibition of contraction at a concentration of $10^{-7}$M (28.5 ng/ml). The inhibition of the electrically induced contractions of the mouse vas deferens showed essentially the same characteristics except that the inhibition was slightly slower in onset and sustained longer. Attempts to block the inhibition with a four-to-ten minute pretreatment with naloxone or naltrexone ($10^{-6}$M), two narcotic antagonists, were unsuccessful.

PROPERTIES OF MLC

Table 2 summarizes the effects of various enzymes and chemical reagents on MLC.

TABLE 2

EFFECT OF CHEMICAL TREATMENTS ON MLC ACTIVITY

| Chemical Treatment | % Loss of RIA Equivalents |
|---|---|
| Pronase .01 mg/ml | 0 |
| Trypsin .01 mg/ml | 0 |
| Carboxypeptidase A. .01 mg/ml | 0 |
| Aminopeptidase .01 mg/ml | 0 |
| 0.1N HCl | 0 |
| $NaIO_3$ | 0 |
| $K_2S_2O_5$ | 0 |
| 0.1N NaOH | 50% |
| $H_2O_2$ | 100% |
| $I_2$ | 100% |

MLC was purified as described in methods. A known amount was then incubated with the peptidases (.01 mg/ml), pronase, trypsin, carboxypeptidase A, aminopeptidase, 0.1N HCl, 0.1N NaOH (boiled for 10 minutes), $NaIO_3$ (0.5 g/ml overnight), $K_2S_2O_5$ (0.1 mg/ml overnight), 1% $H_2O_2$ overnight and 0.2 $NI_2$ for five minutes. Following incubation with the above, the MLC was assayed with the radioimmunassay. When MLC was treated with peptidases, the solution was boiled for 10 minutes to destroy enzymatic activity prior to radioimmunoassay.

None of the peptidases, pronas (Enzyme Development Corp.), trypsin (Sigma), carboxypeptidase A (Worthington Biochem Corp.), and aminopeptidase (Rohm), altered MLC activity as measured by radioimmunoassay or bioassay. Neither activities were altered on incubation overnight at room temperature in 0.1N HCl or on boiling in 0.1N HCl for 10 minutes. Treatment with reducing agents such as $NaIO_3$ (0.5 mg/ml overnight) and $K_2S_2O_5$ (0.1 mg/ml overnight) also had no effect on biologic or immunological activity. However, boiling for 10 minutes in 0.1N NaOH destroyed approximately 50% of the immunological activity as determined by radioimmunoassay, and 1% $H_2O_2$ (overnight) and 0.2N $I_2$ at pH 9.3 for 5 minutes destroyed all the immunological activity. In each case, biological activity was affected to approximately the same extent. An authentic sample of morphine was affected similarly by the oxidizing reagents.

Thin layer chromatography: Both morphine and MLC were chromatographed on thin layer plates in four different solvent systems: (a) butanol-acetic acid-water (4:1:1), (b) chloroform-acetone-diethylamine (5:4:1), (c) chloroform-diethylamine (9:1), and (d) butanol-benzene-methanol-water (15:10:60:15). In all systems, the $R_f$ value for morphine was identical to the $R_f$ value observed for MLC. The $R_f$ value in system (a) was 1.0, for (b) 0.16 and for (c) 0.08 and (d) 0.7. When both substances were co-chromatographed, one spot with an $R_f$ of morphine was obtained. When the chromatogram was sprayed with ferric chloride ferricyanide mixture, a blue color appeared characteristic of a phenol.

DISCUSSION

The data presented here indicate that brain extracts contain a substance (MLC) which effectively binds to morphine specific sites on antibodies generated against the alkaloid. This implies that MLC has certain functional groups which are recognized by the antibody and thus probably bears some resemblance to morphine. The fact that MLC also contains a phenol group and yields the same $R_f$ values as morphine in four different solvent systems, further emphasizes the close similarity to morphine. It should be noted that purified MLC is heat stable and is resistant to dilute acid and a variety of peptidases distinguishing it from the morphine-like peptide, enkephalin, recently reported. MLC is, however, sensitive to oxidation by hyrogen peroxide and iodine, as is morphine. Although MLC is stable when purified, it is quite labile in brain homogenates which explains why it does not ordinarily interfere with the RIA for morphine in brain. Also, because of the small quantities found in brain tissues, the dilutions one uses for RIA eliminate interference from MLC. Like morphine, MLC inhibits the electrically induced contractions of both the guinea pig ileum and the mouse vas deferens. However, unlike morphine the inhibition of electrically induced contractions is not reversed by pretreatment with either naloxone or naltrexone ($10^{-6}M$), two pure narcotic antagonists. The latter might be explained in that either the inhibition produced by MLC is not mediated via the narcotic receptor or that MLC has a far greater affinity for the narcotic receptor than do either the narcotic antagonists or morphine. The latter appears to be so judging from the dose response observed in the bioassay.

It should be pointed out that MLC was assayed by a radioimmunoassay directed against morphine. It may be that the amounts of MLC are more than is indicated by the morphine immuno equivalents. It is also possible that the affinity of the MLC for the antibody could approach that of morphine.

Recently a peptide, enkephalin, was isolated from brain and shown to interact with the opiate receptor. MLC differs from enkephalin in several ways. It is not a peptide as shown by its resistance to peptidases and acid hydrolysis and the distributions of MLC and enkephalin also appear somewhat different. Unlike enkephalin the distribution of MLC in the brain does not exactly parallel the reported distribution of the putative narcotic receptor.

I claim:

1. A morphine-like compound endogenous in mammalian brain tissue having the following physical, chemical and biological properties:
   a. effectively binds to morphine specific antibodies;
   b. non-peptidic as indicated by resistance to peptidases, acid hydroylysis and heat;
   c. has the same $R_f$ as morphine by thin layer chromatography;
   d. exhibits opiate agonist activity as indicated by the guinea pig ileum and mouse vas deferens assays, which activity is not blocked by pretreatment with naloxone or naltrexone;
   e. produces a blue color when treated with a ferric chloride-ferricyanide mixture indicating the presence of a phenolic moiety;
   f. is filterable through a filter having a one thousand molecular weight cutoff, said morphine-like compound being essentially free of other substances normally present in mammalian brain tissue.

2. A morphine-like compound endogenous in mammalian brian tissue prepared by the following process:
   a. treating a methanol extract of mammalian brain tissue with morphine specific antibody so as to form a conjugate between said morphine-like compound and said antibody;
   b. separating said conjugate from said extract by precipitating said conjugate by addition of ammonium sulphate;
   c. separating said morphine-like compound from said antibody by heat denaturization followed by ultrafiltration through a filter having a cutoff of molecular weight one thousand; and
   d. recovering said morphine-like compound from the ultrafiltration filtrate.

* * * * *